United States Patent [19]

Kubota et al.

[11] Patent Number: 5,047,043
[45] Date of Patent: Sep. 10, 1991

[54] RESECTING DEVICE FOR LIVING ORGANISM TISSUE UTILIZING ULTRASONIC VIBRATIONS

[75] Inventors: Tetsumaru Kubota; Tatsuo Nagasaki; Koji Taguchi; Hiroyoshi Fujimori; Akio Nakada; Syuichi Takayama; Daisaku Negoro; Toshiki Terayama; Hiroyuki Kusunoki; Shinji Hatta; Hitoshi Karasawa; Masaaki Hayashi; Tadao Hagino; Akihiro Taguchi, all of Tokyo, Japan

[73] Assignee: Olympus Optical Co., Ltd., Tokyo, Japan

[21] Appl. No.: 449,101

[22] Filed: Dec. 7, 1989

Related U.S. Application Data

[63] Continuation of Ser. No. 233,988, Aug. 15, 1988, abandoned, which is a continuation of Ser. No. 20,445, Mar. 2, 1987, abandoned.

[30] Foreign Application Priority Data

Mar. 11, 1986 [JP] Japan ............................ 61-53219
Mar. 17, 1986 [JP] Japan ............................ 61-58603

[51] Int. Cl.$^5$ ............................................ A61B 17/32
[52] U.S. Cl. .................................................. 606/169
[58] Field of Search ............... 606/160, 161, 169, 171; 128/751, 752, 757, 758, 24 A; 604/22; 433/119; 30/85

[56] References Cited

U.S. PATENT DOCUMENTS

| | | | |
|---|---|---|---|
| Re. 28,752 | 3/1976 | Balamuth et al. | 433/119 X |
| 872,567 | 12/1907 | Langstaff | 606/160 |
| 2,108,758 | 2/1938 | Thompson et al. | 30/85 X |
| 2,714,890 | 8/1955 | Vang | 128/305 |
| 3,861,391 | 1/1975 | Antonevich et al. | 128/328 |
| 3,896,811 | 7/1975 | Storz | 128/328 |
| 3,927,675 | 12/1975 | Pohlman et al. | 128/328 |
| 4,016,882 | 4/1977 | Broadwin et al. | 128/305 |
| 4,188,952 | 2/1980 | Loschilov et al. | |
| 4,221,222 | 9/1980 | Detsch | 606/160 X |
| 4,419,987 | 12/1983 | Ogiv | 128/6 X |
| 4,750,902 | 6/1988 | Wuchinich et al. | 604/22 |

FOREIGN PATENT DOCUMENTS

| | | |
|---|---|---|
| 2256127 | 5/1974 | Fed. Rep. of Germany. |
| 53-11502 | 3/1978 | Japan. |
| 1137072 | 1/1985 | U.S.S.R. |

OTHER PUBLICATIONS

Mueller, "The Surgical Armamentarium", p. 161 (1980).

*Primary Examiner*—Michael H. Thaler
*Attorney, Agent, or Firm*—Frishauf, Holtz, Goodman & Woodward

[57] ABSTRACT

A medical resecting device is disclosed in which, a living organism tissue is resected with ultrasonic vibrations while the corresponding body cavity is observed with an optical observation pipe. The resecting device includes an ultrasonic vibrator for generating ultrasonic vibrations, a horn connected to the vibrator, a probe connected to the front portion of the horn to transmit the ultrasonic vibrations generated by the vibrator, the probe being provided with a rod-like shaft and a distal end portion with a resecting blade, a power source unit for supplying a drive voltage to the vibrator, and an optical observation pipe having a guide hole in which the shaft of the probe is inserted.

5 Claims, 7 Drawing Sheets

F I G. 4
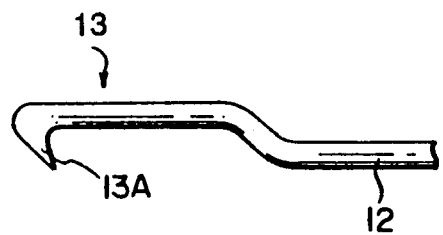
F I G. 5
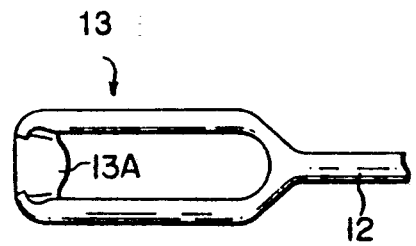
F I G. 6
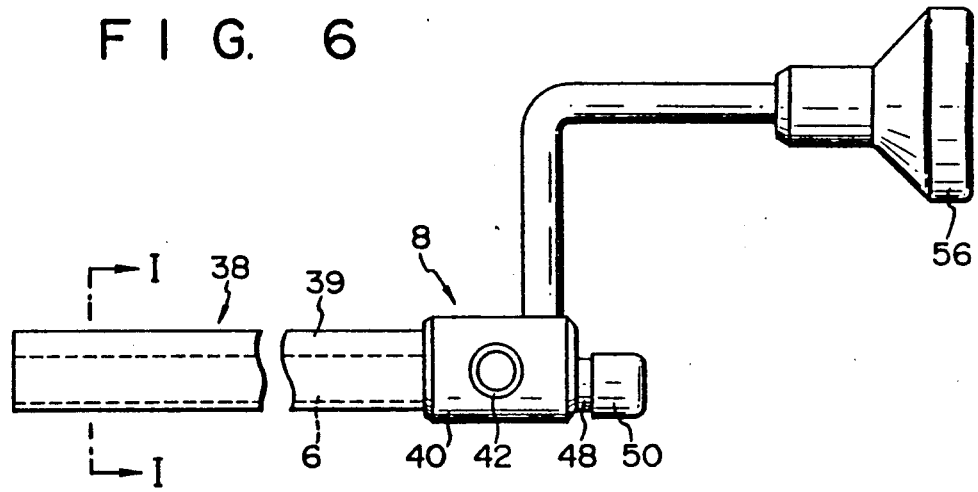

RESECTING DEVICE FOR LIVING ORGANISM TISSUE UTILIZING ULTRASONIC VIBRATIONS

This application is a continuation of application Ser. No. 07/233,988, filed Aug. 15, 1988, abandoned, which in turn is a continuation of Ser. No. 07/020,445 filed Mar. 2, 1987, now abandoned.

BACKGROUND OF THE INVENTION

A. Field of the Invention

The present invention relates to a resecting device for living organism tissue by utilizing ultrasonic vibrations and, more particularly, to a medical resecting device for resecting the living organism tissue with ultrasonic vibrations while the corresponding body cavity is observed with an optical observation pipe.

B. Description of the Prior Art

An endoscope, such as a resectoscope, have been conventionally used in normal observations, diagnoses and therapies for human tissue of interest. For example, by using a resectoscope disclosed in Japanese Patent Disclosure (Kokai) No. 58-81029, an operator resects the tissue of interest while it is cauterized with an RF current.

According to this treatment, however, the cauterized tissue is degenerated into whitish tissue, and thus it is difficult to judge the resection area. The conventional treatment poses a problem wherein even normal tissue tends to be resected. In addition, when an electrode applied with an RF current is erroneously brought into contact with the muscle tissue of a patient, the muscle tissue reacts and is pierced, thereby causing excessive bleeding.

SUMMARY OF THE INVENTION

It is an object of the present invention to provide a resecting device capable of resecting the tissue of interest by using ultrasonic vibrations without damaging the normal tissue while the tissue of interest is observed with an optical observation pipe inserted in a living organism at the time when the tissue of the living organism, e.g., the cartilage tissue is to be resected.

In order to achieve the above object of the present invention, there is provided a treatment device comprising ultrasonic vibration generating means for generating ultrasonic vibrations, a horn connected to the ultrasonic vibration generating means, a probe, connected to a front portion of the horn, for transmitting the ultrasonic vibrations generated by the ultrasonic vibration generating means, the probe being provided with a rod-like shaft and a distal end portion having a resecting blade, a power source unit for supplying a drive voltage to the ultrasonic vibration generating means, and an optical observation pipe having a guide hole into which the rod-like shaft of the probe is inserted.

The resecting device according to the present invention comprises the probe including the rod-like shaft and the distal end portion with a resecting blade, and the optical observation pipe having a guide hole into which the shaft is inserted. Therefore, the operator can resect the tissue of interest without damaging the normal tissue while observing the tissue of interest.

BRIEF DESCRIPTION OF THE DRAWINGS

FIG. 4 is a side view showing a distal end portion of a probe of the resecting unit according to the first embodiment;

FIG. 5 is a plan view of the probe shown in FIG. 4;

FIG. 6 is a side view of an optical observation pipe according to the first embodiment;

DETAILED DESCRIPTION OF THE PREFERRED EMBODIMENTS

Preferred Embodiments of the present invention will be described in detail with reference to the accompanying drawings.

Figure 1:
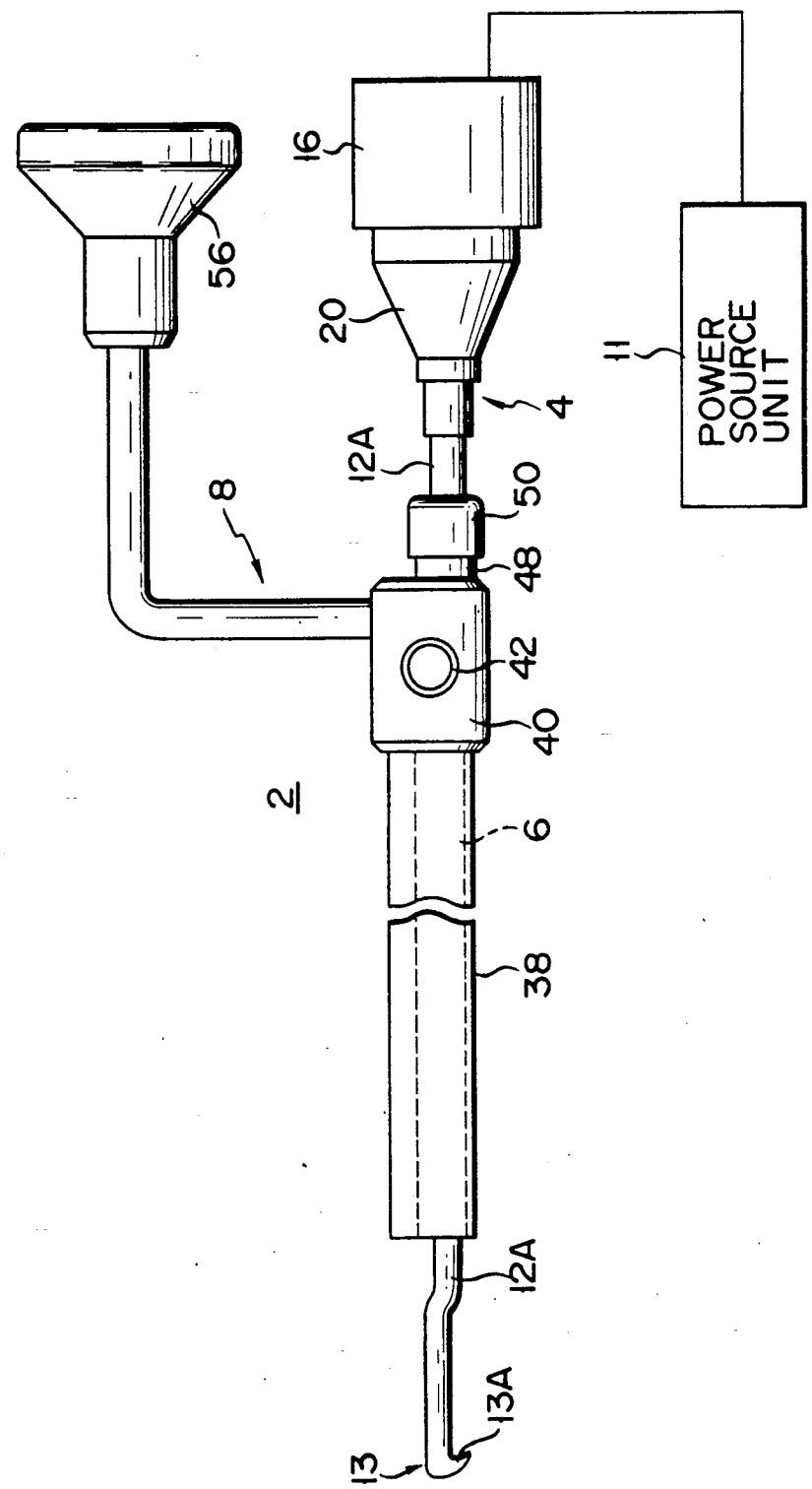
FIG. 1 is a side view of a living organism resecting device utilizing ultrasonic vibrations according to a first embodiment of the present invention.

FIG. 1 illustrates a living organism tissue resecting device utilizing ultrasonic vibrations according to an embodiment of the present invention.

Living organism tissue resecting device 2 comprises resecting unit 4 and optical observation pipe 8. Unit 4 has an ultrasonic vibration generator, and pipe 8 has guide hole 6. Probe 12 of resecting unit 4, having rod-like shaft 12A and a distal end portion, is inserted in hole 6.

Figure 2:
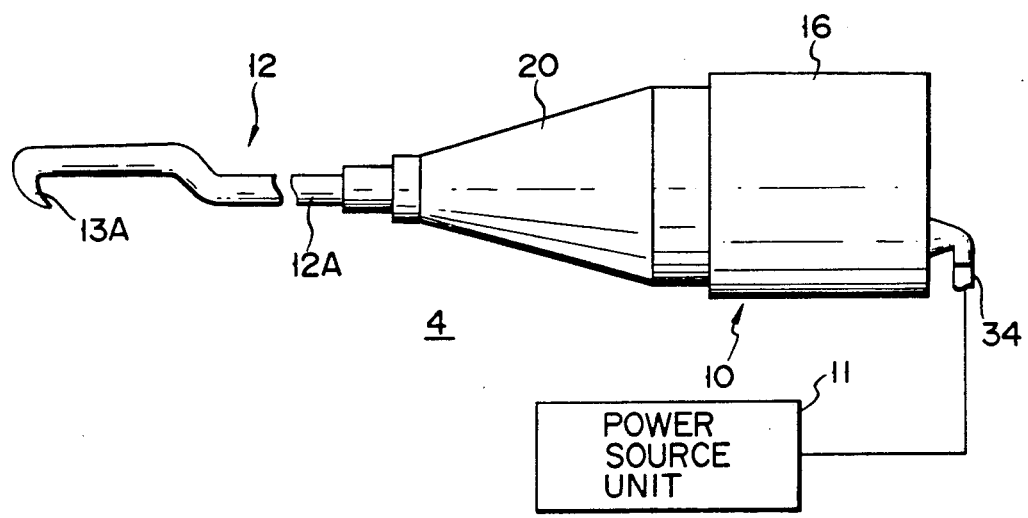
FIG. 2 is a side view showing a resecting unit according to the first embodiment.
Figure 3:
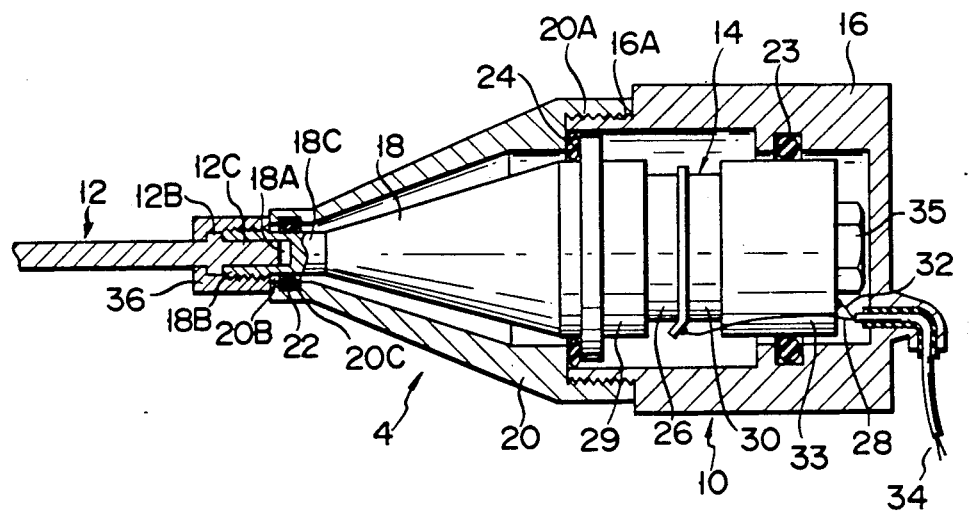
FIG. 3 is a partially cutaway side view of the resecting unit shown in FIG. 2.

Resecting unit 4 comprises handle 10 incorporating the ultrasonic vibration generator therein, probe 12 inserted in guide hole 6, and power source unit 11, as shown in FIG. 2. As is best shown in FIG. 3, handle 10 comprises cup-like outer case 16 for storing ultrasonic vibrator 14 and conical cover member 20 for storing horn 18 disposed in front of vibrator 14. Male threaded portion 16A is formed on the outer surface near the opening of case 16. Cover member 20 has open ends. Female threaded portion 20A is formed on the inner surface of one opening, i.e., a large-diameter opening. Threaded portion 16A is threadably engaged with threaded portion 20A to integrally couple case 16 with cover member 20.

Annular groove 20C is formed on the inner surface of small-diameter opening 20B of cover member 20. O- ring 22 is fitted between annular groove 20C and the outer surface of small-diameter portion 18C of horn 18. Cover member 20 serves as a waterproof cover.

Langevin type ultrasonic vibrator 14 comprises front metal member 29, front electrode 26, piezoelectric element 25, rear electrode 30, and rear metal member 33. These members are tightened by bolt 35. Vibrator 14 is held in case 16 through O-ring 23 and 24. One electrode is connected to power source unit 11 through lead wire 28, the other electrode is connected thereto through lead wire 32. These wires are twisted to constitute single cable 34. Cable 34 is guided outside case 16 from the rear portion thereof.

Small-diameter end portion 18C of horn 18 extends from the end face of small-diameter opening 20B of cover member 20. Male threaded portion 18B is formed on the outer surface of end portion 18C. Connecting hole 18A is formed inside end portion 18C to mount probe 12. Elongated probe 12 comprises proximal end portion 12C and flange portion 12B. Proximal portion 12C is fitted in this connecting hole, and flange portion 12B abuts against the end face of end portion 18C. Thereafter, flange portion 12B is directed by ring nut 36 toward the direction of horn 18, so that probe 12 is fixed to horn 18. In order to remove probe 12 from horn 18, ring nut 36 is loosened and removed. Resecting blade 13 having downwardly extending pawl 13A is formed at the distal end portion of probe 12, as shown in FIGS. 4 and 5. The distal end portion of probe 12 is the widened portion shown in FIG. 5 as extending leftward from the tip of the narrow rod-like shaft portion on the right side of the drawing.

Probe 12 of resecting unit 4 having the structure described above is inserted in guide hole 6 in optical observation pipe 8 shown in FIG. 6. Pipe 8 comprises insertion portion 38 with cylindrical sheath 39 made of a hard material and main body 40 connected to the proximal end of insertion portion 38. Light guide metal piece 42 is formed on main body 40. A light source unit (not shown) is connected to metal piece 42. Illumination light is incident from the light source unit onto metal piece 42 and is transmitted to light guides 44 and 46 shown in FIG. 7. Pipe 48 defining guide hole 6 extends backward through main body 40. Rubber cap 50 is mounted on the end portion of pipe 48 to block the space between the outer surface of probe 12 of resecting unit 4 and the inner surface of pipe 48, as shown in FIG. 1.

Figure 7:
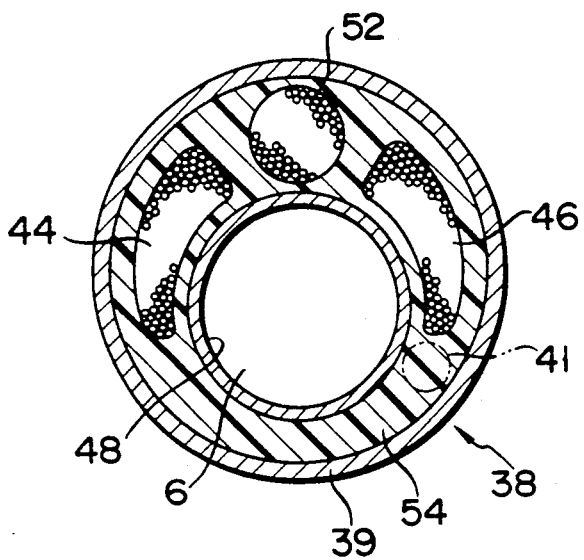
FIG. 7 is a sectional view of the optical observation pipe shown in FIG. 6 taken along the line I—I thereof.

FIG. 7 shows an enlarged section of insertion portion 38 of optical observation pipe 8. Pipe 48 defining guide hole 6 for receiving a probe therein, image guide 52, and light guides 44 and 46 are inserted in sheath 39 in insertion portion 38. These members are fixed in position in sheath 39 by filler member 54. As shown in FIG. 6, eyepiece 56 is arranged at the end portion of pipe 8. The operator can observe the body cavity through eyepiece 56.

A method of operating the living organism tissue resecting device according to this embodiment will be described below.

Figure 8:
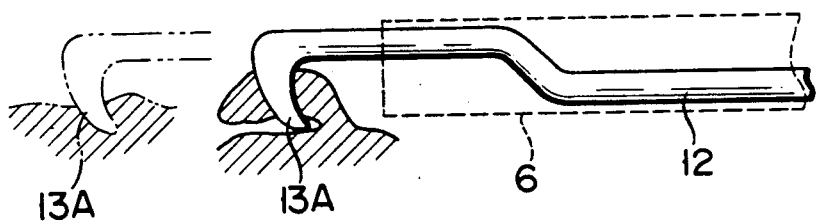
FIG. 8 is a side view showing the probe and the living organism tissue to be resected.

In order to resect the tissue of interest using this device, an insertion aid (not shown) is mounted on the opening of the living organism, and insertion portion 38 is inserted in the living organism through the insertion aid. Pawl 13A of resecting blade 13 in resecting unit 4 is located on the tissue to be resected, as indicated by the alternate long and two short dashed line in FIG. 8 while the tissue of interest is observed from eyepiece 56 of optical observation pipe 8. Thereafter, when a voltage is applied to ultrasonic vibrator 14, ultrasonic vibrations generated by vibrator 14 are amplified by horn 18. The amplified vibrations are transmitted to pawl 13A of resecting blade 13 through probe 12. When the operator pulls resecting unit 4 while pawl 13A is being vibrated, the tissue of interest is resected by pawl 13A, as indicated by the solid line in FIG. 8.

The tissue is not regenerated into whitish tissue at the time of resection of the tissue of interest in the resecting device. The operator can easily discriminate the normal tissue from the tissue to be resected. As a result, the normal tissue is not erroneously resected.

Figure 9:
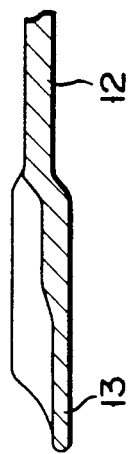
FIG. 9 is a side sectional view showing a modification of the resecting blade of the probe according to the first embodiment.
Figure 10:
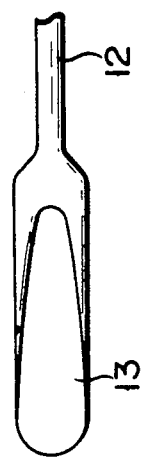
FIG. 10 is a plan view of the resecting blade shown in FIG. 9.
Figure 11:
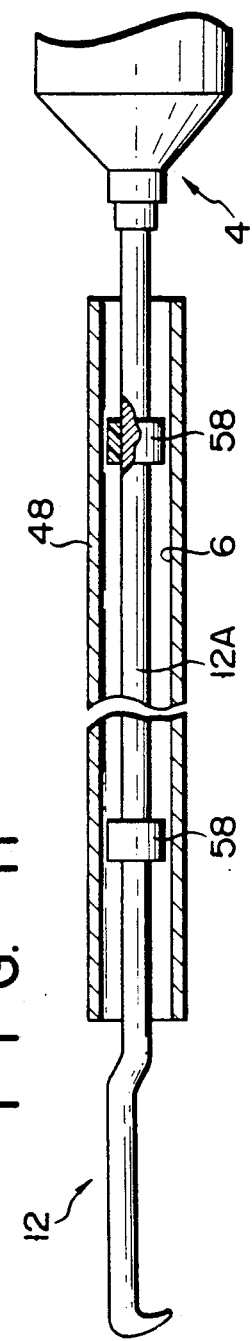
FIG. 11 is a partially cutaway side view showing a modification of the probe according to the first embodiment.

The shape of resecting blade 13 in this embodiment may be the one shown in FIGS. 9 and 10, i.e., substantially a spoon-like shape. Alternatively, as shown in FIG. 11, resin ring 58 made of a low wear material such as ethylene tetrafluoride resin is mounted on the shaft of probe 12 of resecting unit 4, especially a shaft portion which serves as a node of vibration when probe 12 is vibrated with ultrasonic waves. In this case, a frictional resistance between probe 12 and guide hole 6 is reduced, and vibrations generated by the ultrasonic vibrator can be effectively transmitted to resecting blade 13 without loss.

Resin ring 58 may be fixed to the inner surface of guide hole 6.

Second guide hole 41 shown by fictitious outline in FIG. 7 may be additionally formed in sheath 39 of insertion portion 38 to insert a treatment tool excluding resecting unit 4, e.g., forceps.

Probe 12 may be fixed to the distal end portion of horn 18 by means of, for example, brazing. In this case, ultrasonic transmission loss can be further reduced.

Probe 12 may be formed of an annular member having a through hole (not shown), and the through hole may be connected to a suction unit (not shown). In this case, a resected tissue can be discharged outside by the suction unit.

A resecting unit in an ultrasonic resecting device according to another embodiment of the present invention will be described with reference to FIG. 12. The resecting unit of this embodiment has substantially the same structure as that of the above embodiment. The same reference numerals as in the first embodiment denote the same parts in the second embodiment, and a detailed description thereof will be omitted.

Figure 12:
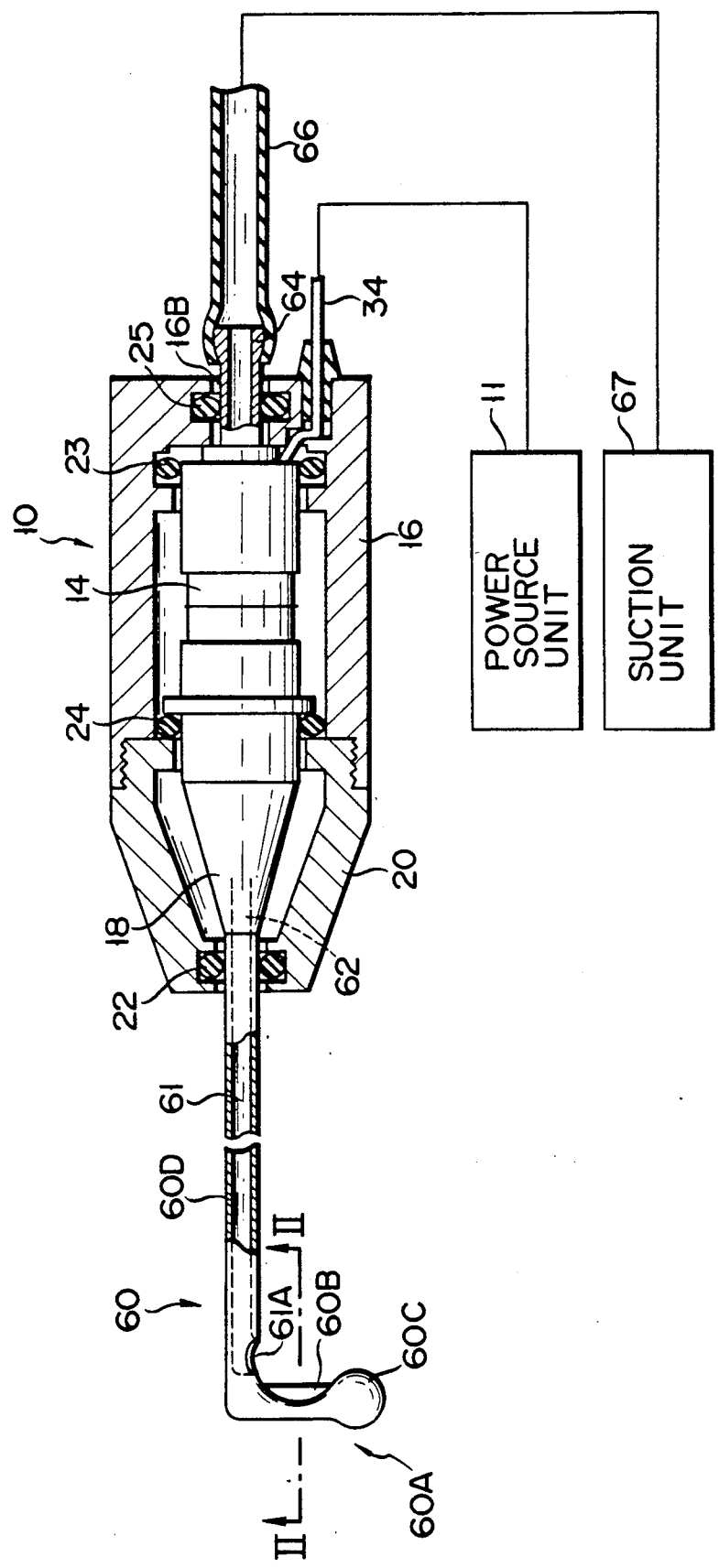
FIG. 12 is a partially cutaway side view of a resecting unit in a living organism tissue resecting device according to another embodiment of the present invention.
Figure 13:
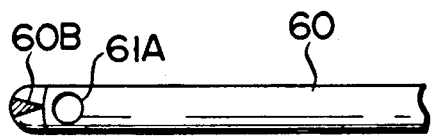
FIG. 13 is a partially cutaway bottom view showing the distal end portion of a probe in the device shown in FIG. 12 taken along the line II—II thereof.

An ultrasonic resecting unit in FIG. 12 has rod 60 corresponding to the probe of the resecting unit of the previous embodiment. Hollow space 61 is defined in rod 60 having rod-like shaft 60D. Space 61 communicates with through hole 62 formed in horn 18. Hole 62 communicates with connecting pipe 64 through vibrator 14. Pipe 64 is disposed in through hole 16B formed in the rear portion of case 16 and is held by O-ring 25. Pipe 64 extends backward from the rear portion of case 16 and is connected to suction unit 67 through tube 66. Electrodes of the vibrator are connected to power source unit 11 through lead wires 34.

The distal end of rod 60 is bent to constitute L-shaped bent portion 60A. Blade element 60B corresponding to the resecting blade of the previous embodiment is contiguous with the rear end of bent portion 60A. Spherical portion 60C having a substantially spherical shape is formed at the distal end of bent portion 60A, and opening 61A of hollow space 61 is located near blade 60B.

An operation of the resecting unit according to this embodiment will be described wherein cartilage tissue formed in, e.g., a knee joint cavity is resected.

A joint position of a knee or the like is pierced to form an aperture. Rod 60 is inserted in the aperture directly or through an insertion aid.

Figure 14:
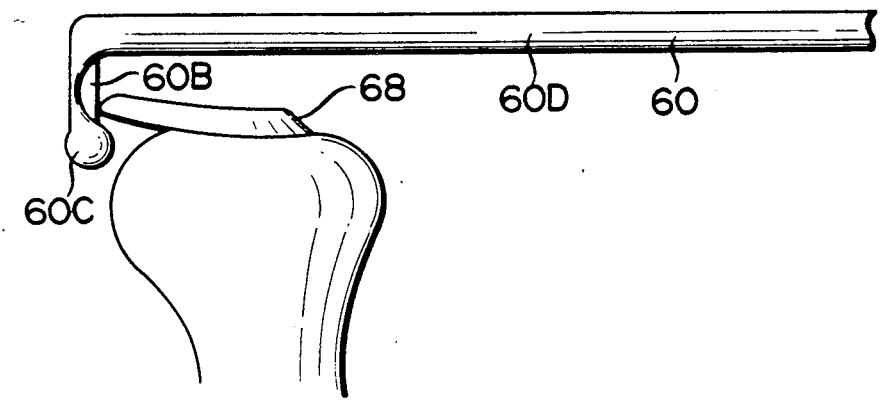
FIG. 14 is a side view showing the distal end portion of the probe shown in FIG. 13 and the cartilage tissue to be resected.

An arthroscope (not shown) has been inserted into the joint cavity from another position. The operator brings the distal end of the rod close the cartilage tissue in the joint cavity, as shown in FIG. 14, while observing the distal end of rod 60 with the arthroscope. Blade 60B formed in rod 60 opposes cartilage tissue 68.

Power source unit 11 is operated to vibrate vibrator 14, and at the same time, suction unit 67 connected to tube 66 is operated.

The ultrasonic vibrations generated by vibrator 14 are amplified by horn 18. The amplified vibrations are transmitted to rod 60. Blade 60B of rod 60, vibrated with ultrasonic waves, is slightly moved back and forth, vertically or laterally to reset cartilage tissue 68.

The resected cartilage tissue is discharged outside by suction unit 67 through hollow space 61 of shaft 60D of rod 60, through hole 62, and tube 66.

Spherical portion 60C having a smooth surface is mounted at the distal end of bent portion 60A of rod 60. Even if the distal end of the rod is erroneously brought into contact with the normal tissue while blade 60B is slightly moved back and forth, vertically or laterally to resect or remove cartilage tissue 68, the distal end is constituted by an arcuated surface. As a result, the normal tissue is not damaged.

Figure 15:
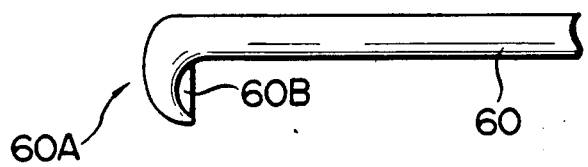
FIG. 15 is a side view showing a first modification of the distal end portion of the probe in the device shown in FIG. 12.

FIG. 15 shows a modification of the rod of the resecting unit according to this embodiment. In this modification, bent portion 60A of rod 60 is arcuated toward the distal end portion.

Figure 16:
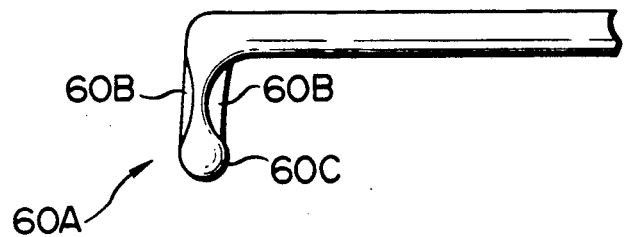
FIG. 16 is a side view showing a second modification of the distal end portion of the probe in the device shown in FIG. 12.

FIG. 16 shows another modification of the rod of the resecting unit according to this embodiment. In this embodiment, bent portion 60A of rod 60 has spherical portion 60C at its distal end, and blade 60B is formed at both sides of bent portion 60A.

Although omitted, a blade and an arcuated portion may be formed at the distal end of the rod, instead of arranging the bent portion thereat.

As described above, the resecting blade is formed at the distal end of the rod vibrated with ultrasonic waves in the resecting unit of the second embodiment, and the smooth arcuated portion is formed at the distal end of the blade. Therefore, the normal tissue is not damaged by the distal end of the blade at the time of resection of the living organism tissue.

What is claimed is:

1. A medical resecting device comprising:
   ultrasonic vibration generating means for generating ultrasonic vibrations;
   a horn coupled to said ultrasonic vibration generating means, said horn having a front portion;
   probe means, coupled to said front portion of said horn, for transmitting ultrasonic vibrations generated by said ultrasonic vibration generating means, said probe means including a rod-like shaft portion and a distal end portion, said distal end portion extending from a tip end of said rod-like shaft portion and including two prongs spaced from each other and extending from said tip end of the rod-like shaft portion, and a resecting blade connected between said prongs, at least a cutting end portion of the resecting blade being at an acute angle with respect to a longitudinal axis of said rod-like shaft portion, said angle being in a given plane and said resecting blade being wider than, in a plane perpendicular to said given plane and parallel to the longitudinal axis, said rod-like shaft portion, said cutting end portion of the resecting blade terminating in an arc-shaped, convex edge facing generally along said longitudinal axis; and
   power source means for supplying a drive voltage to said ultrasonic vibration generating means;
   wherein said probe means has a crank-shaped portion formed between said rod-like shaft portion and said distal end portion, so that the probe means at the tip end of said rod-like shaft portion is bent with the crank-shaped portion in one direction, and said resecting blade is directed in the opposite direction.

2. The device according to claim 1, wherein said rod-like shaft portion, said distal end portion, and said resecting blade are integrally formed as a single unit.

3. The device according to claim 1, further comprising:
   an optical observation tube having a guide hole into which said rod-like shaft portion of said probe is inserted.

4. The device according to claim 1, wherein the prongs extend from said tip end in a direction generally opposite to that in which the rod-like shaft portion extends from its said tip end.

5. A medical resecting device comprising:
   ultrasonic vibration generating means for generating ultrasonic vibrations;
   a horn coupled to said ultrasonic vibration generating means, said horn having a front portion;
   probe means, coupled to said front portion of said horn, for transmitting ultrasonic vibrations generated by said ultrasonic vibration generating means, said probe means including a rod-like shaft portion and a distal end portion, said distal end portion extending from a tip end of said rod-like shaft portion and including two prongs spaced from each other and extending from said tip end of the rod-like shaft portion, and a resecting blade connected between said prongs, at least a cutting end portion of the resecting blade being at an acute angle with respect to a longitudinal axis of said rod-like shaft portion, said angle being in a given plane and said resecting blade being wider than, in a plane perpendicular to said given plane and parallel to the longitudinal axis, said rod-like shaft portion, said cutting end portion of the resecting blade terminating in an arc-shaped, convex edge facing generally along said longitudinal axis, wherein said rod-like shaft portion, said distal end portion, and said resecting blade are integrally formed as a single unit;
   power source means for supplying a drive voltage to said ultrasonic vibration generating means;
   wherein said probe means has a crank-shaped portion formed between said rod-like shaft portion and said distal end portion, so that the probe means at the tip end of said rod-like shaft portion is bent with the crank-shaped portion in one direction, and said resecting blade is directed in the opposite direction, said prongs extending from said tip end in a direction generally opposite to that in which the rod-like shaft portion extends from its said tip end; and
   an optical observation tube having a guide hole into which said rod-like shaft portion of said probe is inserted.

* * * * *